US010580141B2

(12) United States Patent
Freiman et al.

(10) Patent No.: US 10,580,141 B2
(45) Date of Patent: Mar. 3, 2020

(54) VESSEL LUMEN SUB-RESOLUTION SEGMENTATION

(71) Applicant: KONINKLIJKE PHILIPS N.V., Eindhoven (NL)

(72) Inventors: Mordechay Pinchas Freiman, Zichron-Yaakov (IL); Yechiel Lamash, Haifa (IL); Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 280 days.

(21) Appl. No.: 15/542,458

(22) PCT Filed: Jan. 14, 2016

(86) PCT No.: PCT/IB2016/050156
§ 371 (c)(1),
(2) Date: Jul. 10, 2017

(87) PCT Pub. No.: WO2016/113690
PCT Pub. Date: Jul. 21, 2016

(65) Prior Publication Data
US 2018/0276828 A1 Sep. 27, 2018

Related U.S. Application Data (60) Provisional application No. 62/104,100, filed on Jan. 16, 2015.

(51) Int. Cl.
*G06T 7/162* (2017.01)
*G06T 7/00* (2017.01)
*G06T 7/62* (2017.01)

(52) U.S. Cl.
CPC ............ *G06T 7/162* (2017.01); *G06T 7/0012* (2013.01); *G06T 7/62* (2017.01);
(Continued)

(58) Field of Classification Search
CPC ......... G06T 7/162; G06T 7/62; G06T 7/0012; G06T 7/11–12; G06T 2207/20081;
(Continued)

(56) References Cited

U.S. PATENT DOCUMENTS 5,872,861 A 2/1999 Makram-Ebeid
7,876,939 B2 * 1/2011 Yankelevitz ......... A61B 5/1075
382/128

(Continued)

FOREIGN PATENT DOCUMENTS

DE 102009023504 12/2010
WO 2008/065611 6/2008
(Continued)

OTHER PUBLICATIONS

Varma, et al., "Full width at half maximum capacity as a measure of vessel diameter in computed tomography angiography", Proceedings SPIE, vol. 5372, May 4, 2004.
(Continued)

*Primary Examiner* — Michael S Osinski
(74) *Attorney, Agent, or Firm* — Larry Liberchuk (57) ABSTRACT

An imaging system (100) includes a sub-resolution luminal narrowing detector (112) which detects sub-resolution narrowing of a vessel lumen in an image volume by a centerline profile analysis and computes a sub-resolution determined diameter by modifying an approximated visible lumen diameter with the detected sub-resolution narrowing.

12 Claims, 9 Drawing Sheets

(52) U.S. Cl.
CPC ............... *G06T 2207/10081* (2013.01); *G06T 2207/10088* (2013.01); *G06T 2207/10104* (2013.01); *G06T 2207/10132* (2013.01); *G06T 2207/20081* (2013.01); *G06T 2207/20168* (2013.01); *G06T 2207/30048* (2013.01); *G06T 2207/30101* (2013.01); *G06T 2207/30172* (2013.01)

(58) Field of Classification Search
CPC . G06T 2207/20168; G06T 2207/30048; G06T 2207/30172; G06T 2207/10081–10088; G06T 2207/10104; G06T 2207/10088; G06T 2207/10132; G06T 2207/30101–30104; A61B 6/032; A61B 6/504; A61B 6/481; A61B 6/5217; A61B 5/02007; A61B 5/055; A61B 5/1075; A61B 5/026
See application file for complete search history.

(56) References Cited

U.S. PATENT DOCUMENTS

| | | | | |
|---|---|---|---|---|
| 8,600,132 | B2* | 12/2013 | Razifar | A61B 6/032 382/128 |
| 8,675,936 | B2* | 3/2014 | Vija | G06T 5/50 382/128 |
| 9,907,527 | B2* | 3/2018 | Dascal | A61B 6/12 |
| 9,968,409 | B2* | 5/2018 | Yagi | G16H 50/50 |
| 10,349,910 | B2* | 7/2019 | Zhong | A61B 6/5217 |
| 10,373,326 | B2* | 8/2019 | Yoneyama | A61B 5/02014 |
| 2006/0079746 | A1* | 4/2006 | Perret | A61B 5/02007 600/407 |
| 2007/0031019 | A1 | 2/2007 | Lesage | |
| 2007/0197898 | A1* | 8/2007 | Bolle | A61B 5/02007 600/407 |
| 2008/0100621 | A1 | 5/2008 | Kharon | |
| 2008/0119713 | A1* | 5/2008 | Le Nezet | A61B 5/02007 600/407 |
| 2009/0010519 | A1* | 1/2009 | Wakai | G06F 19/321 382/131 |
| 2009/0012382 | A1* | 1/2009 | Dutta | A61B 5/02007 600/407 |
| 2009/0279758 | A1 | 11/2009 | Dikici | |
| 2010/0027862 | A1* | 2/2010 | Kale | G06K 9/4609 382/131 |
| 2010/0298719 | A1 | 11/2010 | Kock | |
| 2012/0082358 | A1* | 4/2012 | Kiraly | G06T 7/0014 382/131 |
| 2012/0236259 | A1* | 9/2012 | Abramoff | A61B 3/12 351/206 |
| 2014/0200867 | A1* | 7/2014 | Lavi | G06T 7/0012 703/2 |
| 2014/0270442 | A1* | 9/2014 | Jung | G06T 7/0012 382/131 |
| 2014/0276011 | A1* | 9/2014 | Schmitt | A61B 5/02007 600/425 |
| 2014/0354794 | A1* | 12/2014 | Imamura | A61B 3/1025 348/78 |
| 2015/0265162 | A1* | 9/2015 | Lavi | A61B 6/5217 600/408 |
| 2015/0282777 | A1* | 10/2015 | Compas | A61B 6/481 600/431 |
| 2016/0174925 | A1* | 6/2016 | Dascal | G06T 7/11 382/130 |
| 2016/0367154 | A1* | 12/2016 | Gladshtein | F16L 33/30 |
| 2017/0007113 | A1* | 1/2017 | Imamura | A61B 3/0025 |
| 2017/0265831 | A1* | 9/2017 | Sankaran | G16H 50/30 |
| 2018/0158201 | A1* | 6/2018 | Thompson | G06T 7/344 |
| 2019/0122401 | A1* | 4/2019 | Senzig | G06T 11/008 |

FOREIGN PATENT DOCUMENTS

| | | |
|---|---|---|
| WO | 2013/121312 | 8/2013 |
| WO | 2014/72861 | 5/2014 |

OTHER PUBLICATIONS

Hu, et al., "Centerline-based vessel segmentation using graph cuts", Proceedings of Sixth International Conference on Graphic and Image Processing, vol. 9443, Oct. 24, 2014.

Gulsun, et al., "Segmentation of carotid arteries by graph-cuts using centerline models", Proceedings of SPIE, vol. 7625, 2010.

Wintermark, et al., "High-Resolution CT Imaging of Carotid Artery Atherosclerotic Plaques", 2008, American Society of Neuroradiology.

Kirbas, et al., "A Review of Vessel Extraction Techniques and Algorithms", Jan. 2003.

Lesage, David, et al. "A review of 3D vessel lumen segmentation techniques: Models, features and extraction schemes." Medical image analysis 13.6 (2009): 819-845.

Kirişli, H. A., et al. "Standardized evaluation framework for evaluating coronary artery stenosis detection, stenosis quantification and lumen segmentation algorithms in computed tomography angiography." Medical image analysis 17.8 (2013): 859-876.

Finegold, et al., "Mortality from ischaemic heart disease by country, region, and age: Statistics from World Health Organisation and United Nations", International journal of cardiology168.2 (2013): 934-945.

Sato, et al., "Accurate quantification of small-diameter tubular structures in isotropic CT volume data based on multiscale line filter responses." Medical Image Computing and Computer-Assisted Intervention—MICCAI 2004. Springer Berlin Heidelberg, 2004. 508-515.—abstract only.

Ford, et al., "Maximal flow through a network." Canadian Journal of Mathematics 8.3 (1956): 399-404.

Edmonds, et al., "Theoretical improvements in algorithmic efficiency for network flow problems." Journal of the ACM (JACM) 19.2 (1972): 248-264.

Goldberg, et al., "A new approach to the maximum-flow problem." Journal of the ACM (JACM) 35.4 (1988): 921-940.

Boykov, et al., "An experimental comparison of min-cut/max-flow algorithms for energy minimization in vision." Pattern Analysis and Machine Intelligence, IEEE Transactions on 26.9 (2004): 1124-1137.

* cited by examiner

VESSEL LUMEN SUB-RESOLUTION SEGMENTATION

CROSS REFERENCE TO RELATED APPLICATIONS

This application is the U.S. National Phase application under 35 U.S.C. § 371 of International Application No. PCT/IB2016/050156, filed Jan. 14, 2016, published as WO 2016/113690 on Jul. 21, 2016, which claims the benefit of U.S. Provisional Patent Application No. 62/104,100 filed Jan. 16, 2015. These applications are hereby incorporated by reference herein.

FIELD OF THE INVENTION

The following generally relates to medical imaging, and is described with particular application to segmentation of luminal structures.

BACKGROUND OF THE INVENTION

The literature has indicated that coronary artery disease is the single largest cause of death worldwide. Coronary artery disease is the narrowing of the lumen of the coronary artery, which supplies oxygen via blood to heart muscle. The lumen of the coronary artery varies in diameter. For example, a left main coronary artery lumen of a healthy adult individual is typically 4.5±0.5 mm in diameter and a distal left anterior descending coronary artery lumen is typically 1.9±0.4 mm.

One non-invasive technique to assess the narrowing of the coronary lumen, e.g. stenosis, is cardiac computed tomography angiography (CCTA). In CCTA, one or more three dimensional (3D) images, e.g. computed tomography (CT) images, of the coronary artery are used to identify and quantify the narrowing of the lumen. Another quantitative measure uses a difference in pressures with fractional flow reserve (FFR) simulations based on a 3D model of the lumen.

Visible imaging resolution or precision, such as with the CCTA imaging, is typically about 1.5 mm, e.g. one spatial dimension that differences in the image can accurately be resolved. Using images to determine the narrowing of a lumen that is less than three to four times the visible resolution impacts first, whether a narrowing is detected and second, the accuracy of a structure of the lumen segmented to quantify measurements affected by narrowing. Reconstruction algorithms typically smooth the image with a low-pass filter, which blurs the lumen boundary. In cases where the lumen diameter is smaller than the low-pass filter support, the smoothing process can cause segmentation algorithms to overestimate lumen diameter. Calcium deposits in an artery narrows the artery, which can cause blooming artifacts in imaging and in typical segmentation algorithms that mimic larger lumens than the true underlying lumens.

SUMMARY OF THE INVENTION

Aspects described herein address the above-referenced problems and others.

The following describes a system and method to detect sub-resolution narrowing of a vessel lumen and to segment the vessel lumen with an improved graph using a graph min-cut algorithm.

In one aspect, an imaging system includes a sub-resolution luminal narrowing detector, which detects sub-resolution narrowing of a vessel lumen in an image volume by a centerline profile analysis and computes a sub-resolution determined diameter by modifying an approximated visible lumen diameter with the detected sub-resolution narrowing.

In another aspect, a method of segmenting a lumen vessel includes detecting sub-resolution narrowing with a centerline profile analysis of an approximated visible lumen diameter in a vessel lumen in an image volume. A sub-resolution determined diameter is computed by modifying the approximated visible lumen diameter based on the detected sub-resolution narrowing.

In another aspect, an imaging system includes a graph min-cut variation segmenter which constructs a graph with each voxel in a segmented region of an image volume represented by a node. Each node is connected to a lumen node and a background node. Edges connecting each node to the lumen node are weighted with a product of a likelihood, $L_i$, the voxel is part of the segmented vessel lumen according to an intensity of a closest centerline voxel and a trained model, and a likelihood, $L_d$, the voxel is part of the segmented vessel lumen based on a spatial distance of the voxel from a closest centerline point and a sub-resolution determined diameter. Edges connecting each node to the background node are weighted by $1-L_i*L_d$. Edges between neighboring voxels are weighted by a smoothness penalty. The graph min-cut variation segmenter cuts the graph, which separates the graph into a first portion connected to the lumen node and a second portion connected to the background node based on a minimal cost and the nodes in the first portion to generate a volume of a segmented vessel lumen.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
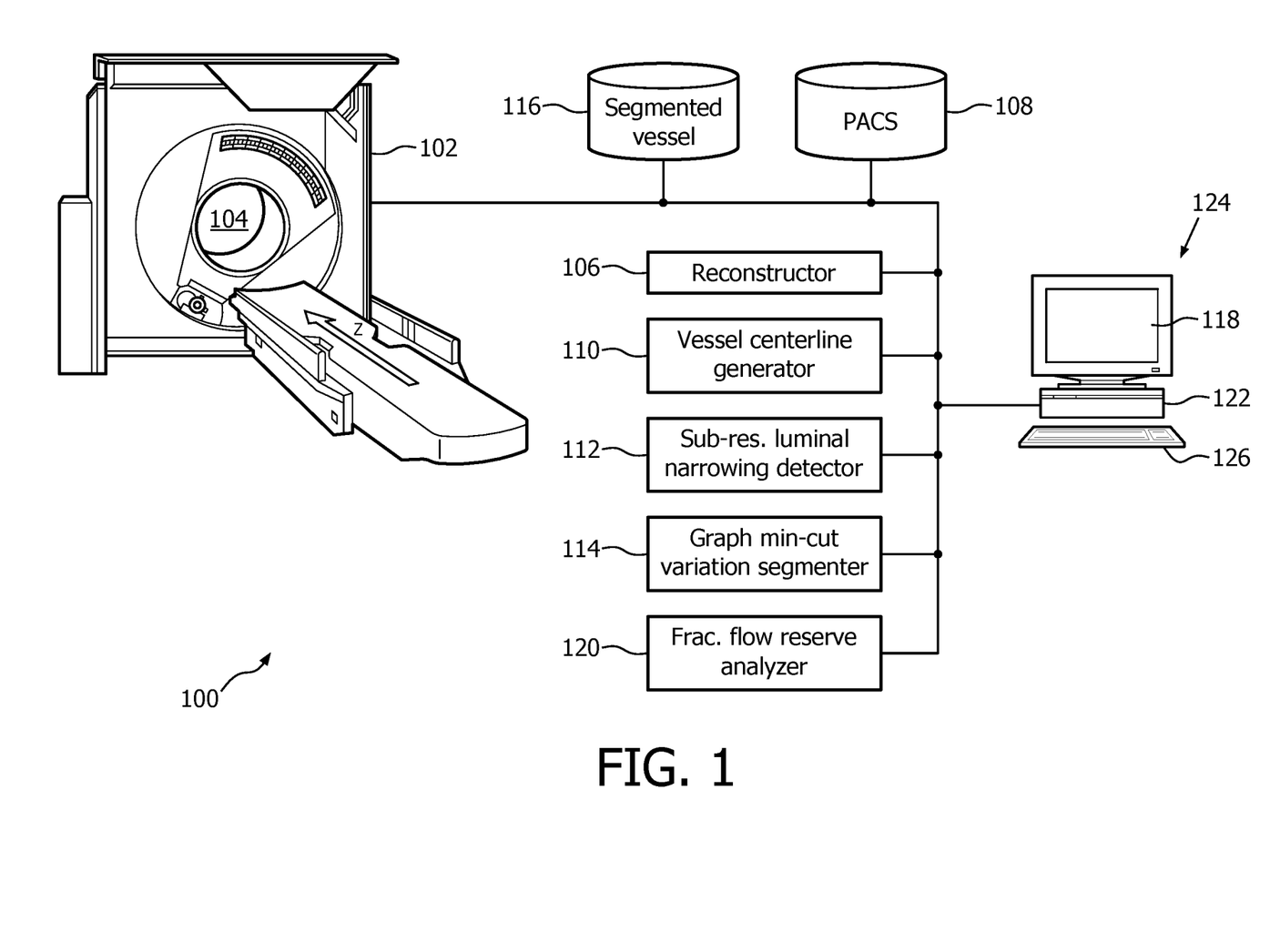
FIG. 1 schematically illustrates an example sub-resolution luminal narrowing detection and segmentation system, in connection with an imaging system.

Initially referring to FIG. 1, an example sub-resolution luminal narrowing detection and segmentation system 100 is illustrated. An imaging device 102 such as a computed tomography (CT) imaging device, ultrasound (US), magnetic resonance imaging (MRI), positron emission tomography (PET), single proton emission computed tomography (SPECT) and the like, generates imaging data, e.g. projection data, raw data, and the like of region of interest of a subject, in an imaging aperture 104 of the imaging device 102 and the region of interest includes structures with lumens, e.g. vascular structures, within a resolution of the imaging device. A reconstructor 106 receives the imaging data, and reconstructs one or more images, e.g. reconstructed image volume(s), from the imaging data. For example, a CT imaging device generates cardiac CT angiography (CCTA) images. The reconstructed image can be received from the imaging device 102 and/or from storage 108, such as a Picture Archiving and Communication System (PACS), Radiology Information System (RIS), Hospital Information System (HIS), Electronic Medical Record (EMR), and the like.

A vessel centerline generator 110 generates a centerline through the lumen of the vessel selected to be segmented. The vessel centerline generator 110 can use techniques known in the art, to generate the centerline of an indicated vascular structure, such as the coronary artery, and/or other techniques. The vessel centerline generator 110 receives the reconstructed image and from the received image either automatically or manually directed determines a centerline of a vessel lumen from the image volume.

A sub-resolution (sub-res.) luminal narrowing detector 112 approximates a visible lumen diameter based on the image volume and the determined centerline. The sub-resolution luminal narrowing detector 112 detects sub-resolution narrowing, e.g. measurement of luminal narrowing with precision greater than the visible resolution of the reconstructed image, with a centerline intensity profile analysis. The centerline intensity profile analysis includes detecting sub-resolution narrowing according to changes in intensity profiles and increased intensities indicative of calcium blooming. The sub-resolution luminal narrowing detector 112 modifies the approximated visible lumen diameter to a sub-resolution determined diameter based on the detected narrowing.

A graph min-cut variation segmenter 114 segments, in one non-limiting instance, the lumen at sub-resolution based on a voxel-wise intensity-based likelihood, a voxel-wise diameter-based likelihood, a smoothness penalty, and an optimization.

The voxel-wise intensity based likelihood for each voxel is computed using a trained model of characteristics of voxel intensities in cross-sections to the centerline. Each voxel in a segmentation region, e.g. the region of the vessel, is assigned a value, $L_i$, representing the likelihood that the voxel is part of the lumen according to an intensity of the closest centerline voxel and the trained model. An intensity of a closest centerline voxel, $I_{ctr}$, is used by the trained model to compute a maximum intensity threshold, $f_{max}(I_{ctr})$, and a minimum intensity threshold, $f_{min}(I_{ctr})$. The likelihood of the voxel is part of the segmented lumen can include the function: $L_i=1/(W_{shu}*((I_{voxel}-I_{ctr})/((f_{max}(I_{ctr})-f_{min}(I_{ctr}))/2))$, where $W_{shu}$ is a weight, and $I_{voxel}$ is the voxel intensity.

The voxel-wise diameter based likelihood for each voxel is computed using the trained model of characteristics of voxel intensities in cross-sections to the centerline. Each voxel in a segmentation region is assigned a value, $L_d$, representing the likelihood that the voxel is part of the lumen based on a spatial distance of the voxel from a closest centerline point and the sub-resolution determined diameter. The likelihood the voxel is part of the segmented lumen based on distance can include the function:

$$L_d = 1 / \left( W_d * \left( \frac{d_{voxel}}{\frac{D}{2}} \right) \right),$$

where $W_d$ is a weight, $d_{voxel}$ is a spatial distance between a voxel and the closest centerline point, and D is the sub-resolution determined diameter at the centerline point.

The smoothness penalty is computed based on a product of local intensity differences, surface direction, and local intensity difference direction pairwise for neighboring voxels, p and neighbor q and the trained model. The local intensity difference for each pair of neighboring voxels can be given by e $$-\left( \frac{(I_p - I_q)^2}{d_{p,q} f_{var}(I_{ctr,p})^2} \right),$$

where $I_p$ and $I_q$ are the intensities of the neighboring voxels in Hounsfield Units (HU), $d_{p,q}$ is the spatial distance between the voxels p and q, $f_{var}(I_{ctr,p})$ is a function from the trained model of the variance of the intensities in HU at the closest centerline point top. The surface direction can be given by $$e^{-\left( \frac{(1-abs((p-q)*dir(ctr,p)^2)}{\theta^2} \right)},$$

where abs is an absolute value function, (p-q) is a vector between voxels p and q, dir(ctr,p) is a direction of the centerline at the closest centerline point to p, and θ is a constant, such as in a range of 0.1 to 0.5 such as 0.3, and/or other value. The local intensity difference direction is given by: 1, if $I_p-I_q>0$ or p(q)>m, where m is a constant of a predetermined threshold maximum intensity, such as a value in a range of 400-800 HU such as 600 HU; and otherwise is 0.

The optimization assigns a label to each voxel in the segmented region as a value representing whether a voxel is in the segmented lumen or not, e.g. background, based on a cut of a constructed graph with a minimal cost that separates the graph into a lumen and a background. The graph includes each voxel represented by a node, and two additional nodes represent the lumen and the background, e.g. non-lumen. Each voxel node is connected to the lumen node and background node by edges. The weight of an edge between each voxel and the lumen node is given by $L_i*L_d$, where $L_i$ and $L_d$ are the likelihood values assigned to the voxel based on intensity and distance described above. The weight of the edge between the each voxel and background node is given by $1-L_i*L_d$. The node of each voxel is connected to nodes of neighboring voxels, e.g. a predetermined set of neighboring voxels such as those that abut the voxel, by an edge weighted by the smoothness penalty as a product of the local intensity difference, surface direction, and local intensity difference direction. The cut of the constructed graph, which includes nodes and weighted edges is performed using a min cut algorithm, such as Ford-Fulkerson, Edmonds-Karp, Push-Relabel, Boykov-Kolmogorov, and the like.

The graph min-cut variation segmenter 114 segments the lumen at sub-resolution based on the assigned label from the min-cut algorithm. The voxels in the cut portion connected to the lumen are defined as a sub-resolution segmented lumen 116. The voxels in the cut portion connected to the background are not included in the segmented lumen. The sub-resolution segmented lumen can be displayed on a display device 118, superimposed on the image volume, and/or stored with the image data 108.

A fractional (frac.) flow reserve analyzer 120 can compute a fractional flow reserve based on the sub-resolution segmented lumen 116. The fractional flow reserve analyzer 120 uses a more accurately segmented structure, e.g. more precise segmented structure, to determine the factional flow reserve, which includes the sub-resolution narrowing according to reduced intensity and/or calcium blooming. The computed fractional flow reserve can be displayed on the display device 118 and/or stored in a computer memory, such as with the image data.

The reconstructor 106, the vessel centerline generator 110, the sub-resolution luminal narrowing detector, the graph min-cut variation segmenter 114, and the fractional flow reserve analyzer 120 are suitably embodied by one or more configured data processors 122, such as an electronic data processor, an optical data processor, a microprocessor, a digital processor, and the like. The configured data processor 122 executes computer readable instructions stored in a non-transitory computer readable storage medium ("memory"). The configured data processor 122 may also execute one or more computer readable instructions carried by a carrier wave, a signal or other transitory medium. The data processor 122 can be comprise a computing device 124, such as a workstation, laptop, mobile computing device, smartphone, server, body worn computing device, and the like. The data processor 122 can be a distributed computing device, such as peer-to-peer computing devices, client-server computing devices, and the like.

The computing device 124 can include the display device 118, such as a Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display, and the like. The computing device 124 can include one or more input devices 126, such as a keyboard, microphone, mouse, touch screen, and the like.

Figure 2:
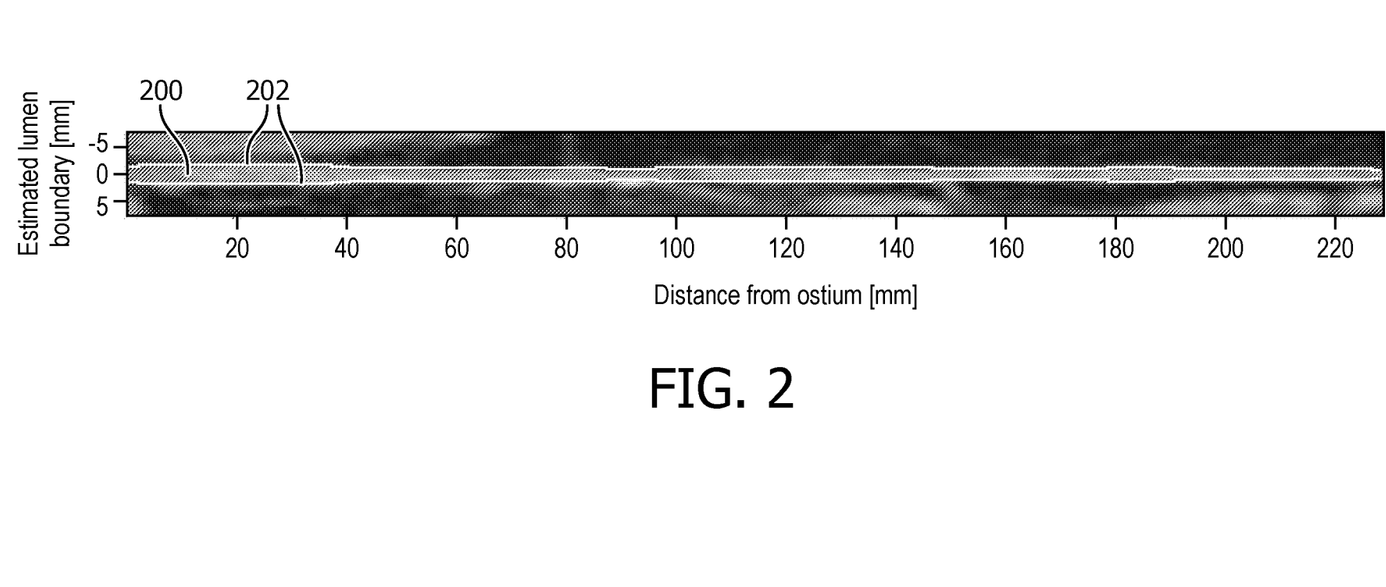
FIG. 2 illustrates an example of an approximated lumen diameter using Full-Width Half-Maximum (FWHM) rule.

With reference to FIG. 2, an example of an approximated visible lumen diameter determined using a Full-Width Half-Maximum (FWHM) rule is illustrated. A left anterior descending coronary lumen 200 is shown in a straight multi-planar view. The view uses the distance from the generated centerline on the vertical axis in millimeters (mm) and the distance from an ostium on the horizontal axis in millimeters. The approximated visible lumen diameter 202 is indicated as a white line.

Rays in planes perpendicular to the centerline at different angles are sampled for intensity values. The full width half maximum (FWHM) rule is applied to determine an approximate visible diameter for each sampled ray. The FWHM selects the diameter end points where the intensity values are half the maximum or peak intensity value and a maximum width of an intensity distribution curve. A diameter value, such as a median value, over the sampled rays in each plane is computed for each cross section to determine the approximated visible lumen diameter. In one instance, a mean value of the sample rays is computed for the diameter value. A filter can smooth the diameter values across the planes perpendicular to the centerline.

Figure 3:
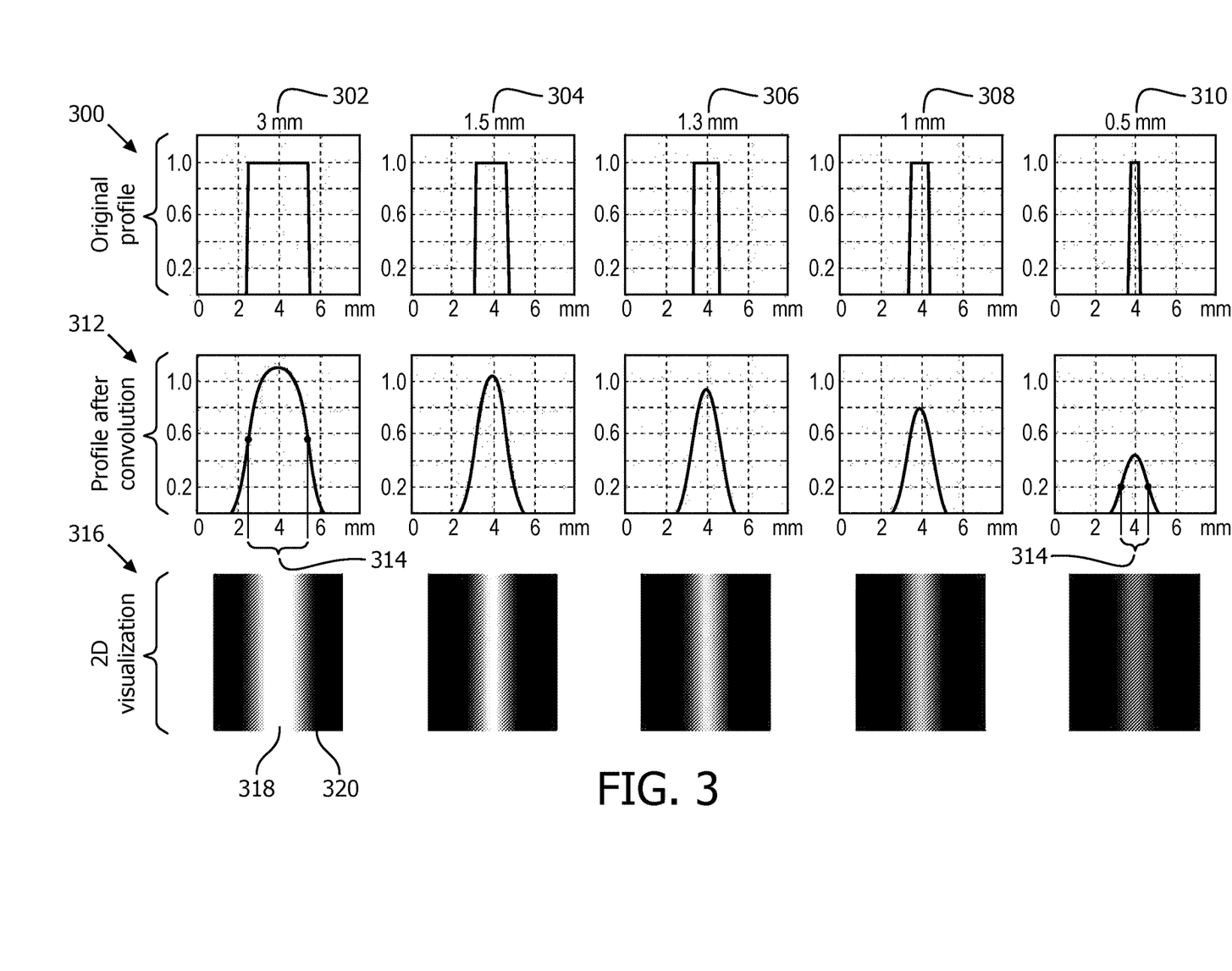
FIG. 3 schematically illustrates examples of visualization of varying vessel diameters at visible imaging resolution.

With reference to FIG. 3, examples of visualization of varying vessel diameters at visible imaging resolution are schematically illustrated. Vessel diameters are overestimated based on the reconstructed image. Lumen profiles 300, e.g. true dimensions, are illustrated with different profiles or diameters of 3 mm 302, 1.5 mm 304, 1.3 mm 306, 1 mm 308, and 0.5 mm 310. The dimensions are shown on the horizontal axis with a centerline at 4 mm and an intensity of 1.0 on the vertical axis. Lumen profiles after convolution 312, e.g. as viewed through an imaging device at resolution, are shown corresponding to each of the true lumen profiles. The lumen profiles after convolution use the same axis as the true lumen profiles. As the diameter is narrowed, a measurement of the intensity profile 314 after convolution is reduced, such as indicated by a peak, a width, a shape and/or the FWHM (defined above) measurement. For example, the peak intensities of the lumens in order of decreasing size are approximately 1.1, 1.0, 0.9, 0.8, and 0.4. The width at half maximum, e.g. dimensions at intensities of 0.55, 0.5, 0.45, 0.4 and 0.2 in the profiles after convolution respectively, overestimates the true lumens.

Two-dimensional (2D) visualizations 316 of the lumens are illustrated corresponding to each of the different diameter lumens. A first region of intensities indicated in white represents the lumen 318 and a second region of intensities indicated by a dark area represents the non-lumen 320. As visualized and as the diameter of the lumen decreases, the first region is reduced or narrowed, and the intensities of the lumen 318 as represented in the visualization similarly is reduced.

Figure 4:
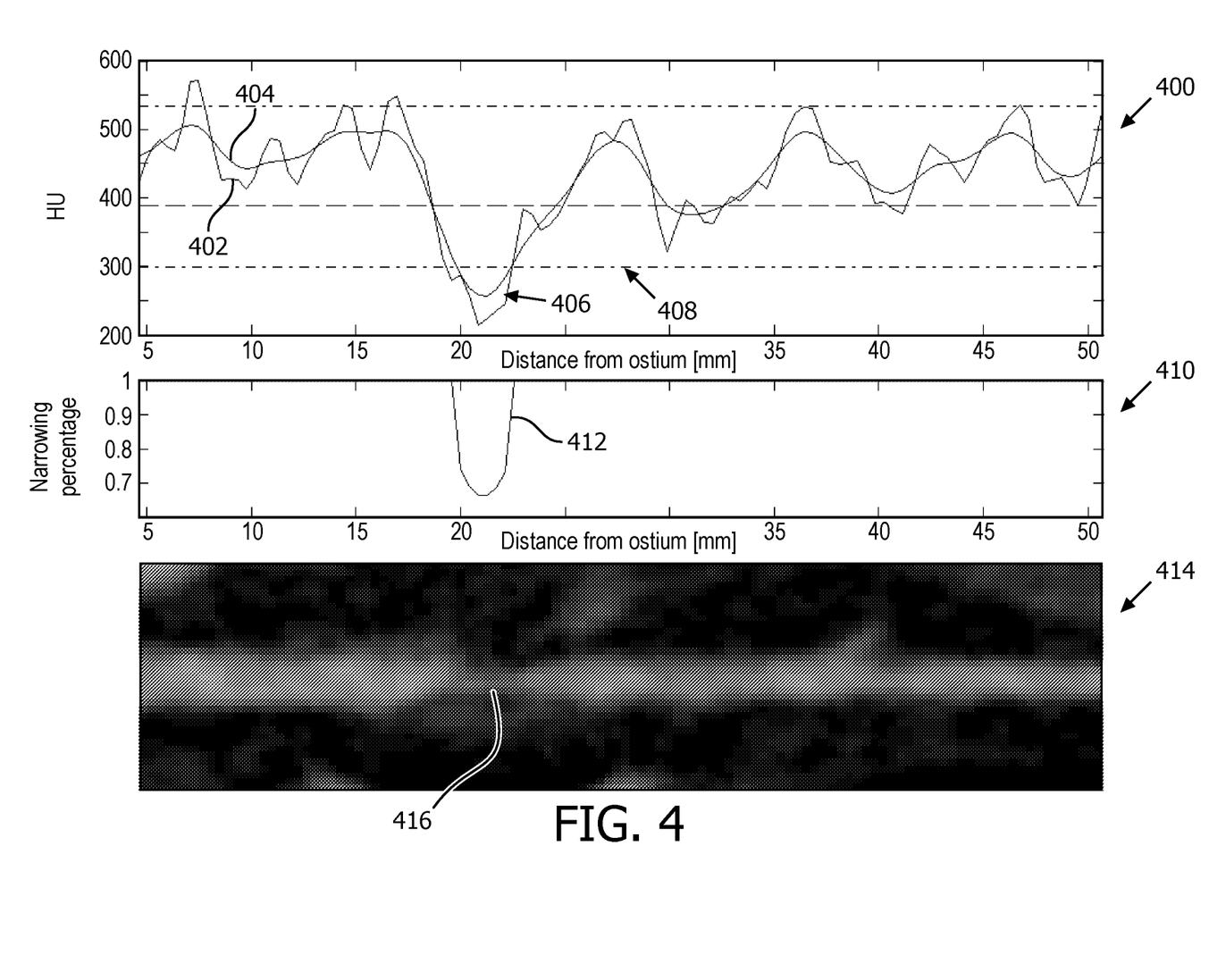
FIG. 4 shows an example graphically of reduced intensity luminal narrowing.

With reference to FIG. 4, a graphical example of reduced intensity luminal narrowing is shown. A first graph 400 depicts an intensity values in HU along the centerline. The vertical axis or y-axis is the intensity value in HU and the horizontal axis or x-axis is a distance along the centerline from the ostium. A first plot on the graph is the intensity values along the centerline 402 and a second plot is a smoothing of the intensity values 404. A narrowing 406 is indicated by a decrease in intensity values, e.g. below a minimum threshold 408, at a distance from the ostium along the centerline between 19 mm and 23 mm. The minimum threshold 408 is based on the centerline intensity values, such as the median centerline intensity value.

The sub-resolution luminal narrowing detector 112 computes a multi-scale second order derivative of the centerline profile, e.g. second order derivate of the smoothed line 404 representing the intensity values along the centerline. Narrowing 406 is detected where the values, e.g. line, are below the threshold and the second derivate is positive, e.g. >0.

A second graph 410 depicts the narrowing 412 as a percentage on a vertical axis and the distance from the ostium along the centerline on the horizontal axis, the same scale as the first graph 400, based on the change in intensity values as described in reference to FIG. 3. A corresponding image 414 is displayed, which includes a decreased intensity area 416, e.g. darkened area or less bright area, corresponding to the detected narrowing by the sub-resolution luminal narrowing detector 112 based on intensity values along the centerline. The corresponding image 414 includes the same horizontal axis as the first graph 400 and the second graph 410. In one instance, the sub-resolution luminal narrowing detector 112 receives input from the input device 126 indicating areas to search for narrowing and/or areas presenting narrowing.

The sub-resolution luminal narrowing detector 112 computes a sub-resolution determined diameter from the approximated visible lumen diameter based on the detected narrowing. The computation can include the formula $$D_{sub} = D_{approx} * \alpha\left(\beta\frac{I_{ctr}}{\mu_0} - \gamma\right),$$

where $D_{sub}$ is the diameter of the sub-luminal narrowing, $D_{approx}$ is the approximated visible luminal diameter, $I_{ctr}$ is the intensity value of the centerline, $\mu_0$ is a reference luminal intensity value, such as an intensity value of an aorta, and $\alpha$, $\beta$ and $\gamma$ are constants, such as 0.5, 0.16 and 0.14, respectively.

Figure 5:
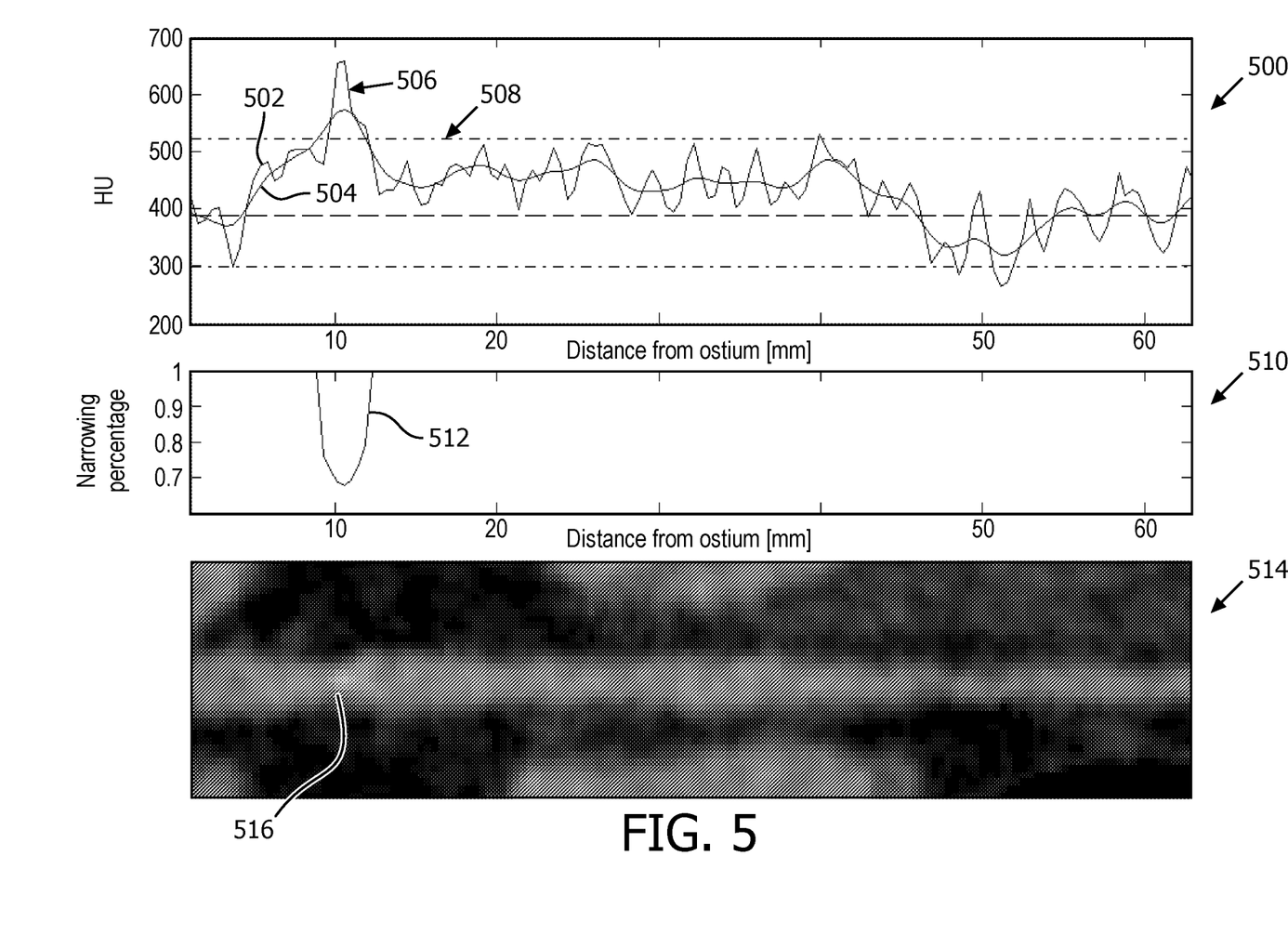
FIG. 5 shows an example of calcium blooming luminal narrowing.

With reference to FIG. 5, an example of calcium blooming with luminal narrowing is shown. The sub-resolution luminal narrowing detector 112 detects narrowing due to calcium blooming based on intensity values greater than a threshold. The first graph 500 includes a line 502 representing intensity values along the centerline, and a second line 504 representing intensity values smoothed with a filter. The intensity values are represented on the vertical axis or y-axis and the distance along the centerline on the horizontal axis or x-axis. Intensity values 506 exceeding a threshold 508 are indicated between 9 mm and 12 mm from the ostium.

The sub-resolution luminal narrowing detector 112 detects narrowing of calcium blooms where the values, e.g. line, are above the maximum threshold 508 and the second derivate is negative, e.g. <0. The intensity value for the upper threshold can use a reference value, such as the intensity of the aorta. The sub-resolution luminal narrowing detector 112 modifies the approximated visible resolution diameter to a sub-resolution determined diameter based on the detected narrowing due to calcium blooming.

A second graph 510 indicates the narrowing 512 as a percentage of the lumen on a vertical axis or y-axis and the distance from the ostium along the centerline on the same horizontal axis as the first graph 500. A corresponding image 514 is displayed, which includes an increased intensity area 516, e.g. brighter area, in the 9 to 12 mm distance corresponding to the detected narrowing due to calcium blooming. The corresponding image 514 includes a common horizontal axis with the first graph 500 and the second graph 510.

Figure 6:
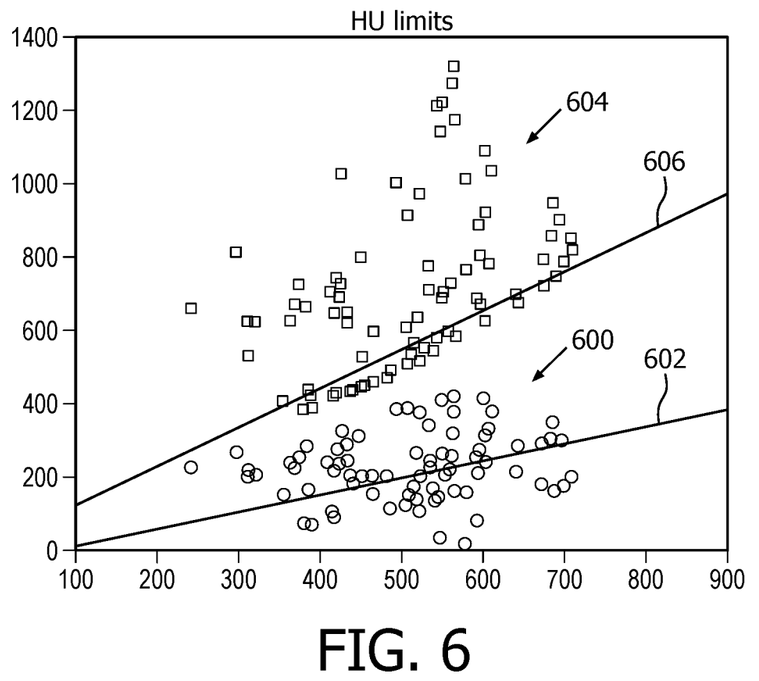
FIG. 6 shows an example graphically of minimum and maximum threshold intensities at luminal cross sections with a fitted linear model.

With reference to FIG. 6, an example graphically of minimum threshold intensities 600 at luminal cross sections with a fitted linear function 602 of a model and maximum threshold intensities 604 at luminal cross sections with a fitted linear function 606 of the model are shown. The graph min-cut variation segmenter 114 generates the model which defines voxel specific intensity limits used in segmenting the lumen based on intensity characteristics of cross sections along the centerline.

The graph min-cut variation segmenter 114 samples characteristic intensities of voxels in cross sections along the centerline. For example, at each cross section, characteristics of a minimum, a maximum, and a standard deviation of the intensities in a region to be segmented are computed. FIG. 6 is a scatter plot with the centerline intensities in HU on the horizontal axis or x-axis, and the maximum and minimum intensities in HU on the vertical axis or y-axis.

The graph min-cut variation segmenter 114 generates the model based on the sampled characteristics. The model includes functions of the centerline intensity. The maximum intensities 606 are darkened and a first function 606 is fitted to the maximum intensities to derive a maximum intensity threshold limit. The first function 606 can include the form $f_{max}=aI_{ctr}+b$, where $f_{max}$ is the maximum intensity threshold of voxels in a plane perpendicular to the centerline bounded by the computed sub-resolution determined diameter, $I_{ctr}$ is the intensity of the voxel at the centerline, and a and b are constants computed through linear regression analysis. The minimum intensities 600 are lighter and a second function 602 is fitted to the minimum intensities 600 to derive a minimum intensity threshold. The second function 602 can include the form $f_{min}=cI_{ctr}+d$, where $I_{min}$ is the minimum intensity of voxels in a plane perpendicular to the centerline, $I_{ctr}$ is the intensity of the voxel at the centerline, and c and d are constants computed through linear regression analysis. The model is different from global values, such as a value derived from aorta intensity or a value derived from values of the centerline, such as a mean of centerline values.

Figure 7:
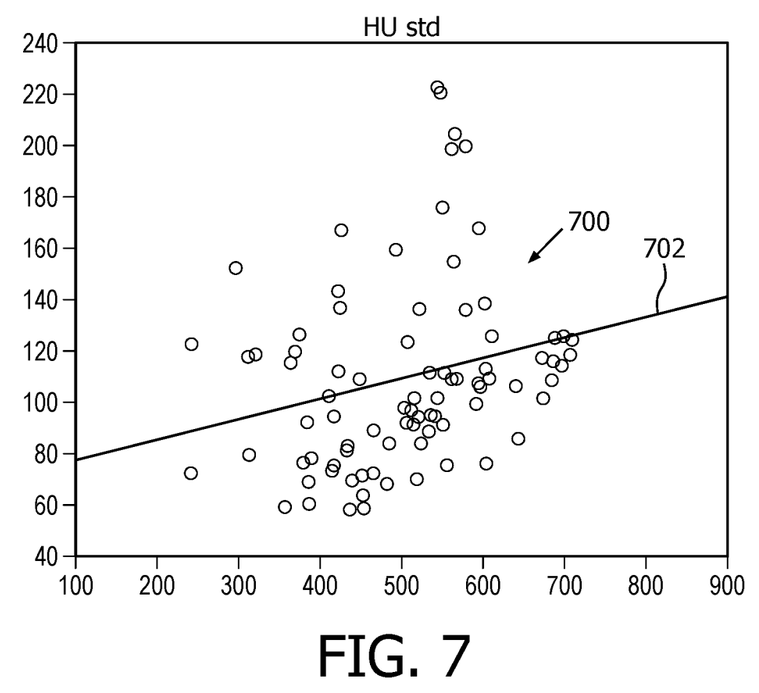
FIG. 7 shows an example graphically of variances threshold intensities of luminal cross sections with a fitted linear model.

With reference to FIG. 7, a graphical example of plotted variance intensities 700 of luminal cross sections and a fitted linear function 702 are shown. The model includes the fitted function 702 of the variances of the sampled centerline cross section intensities. The centerline intensities are represented on the horizontal axis or x-axis in HU, and the variance, e.g. standard deviation, are represented in HU on the vertical axis or y-axis. A third function 702 is fitted to the sampled variances. The third function 702 can include the form $f_{var}=eI_{ctr}+f$, where $I_{var}$ is the variance of intensity of voxels in a plane perpendicular to the centerline, $I_{ctr}$ is the intensity of the voxel at the centerline, and e and f are constants computed through linear regression analysis.

Figure 8:
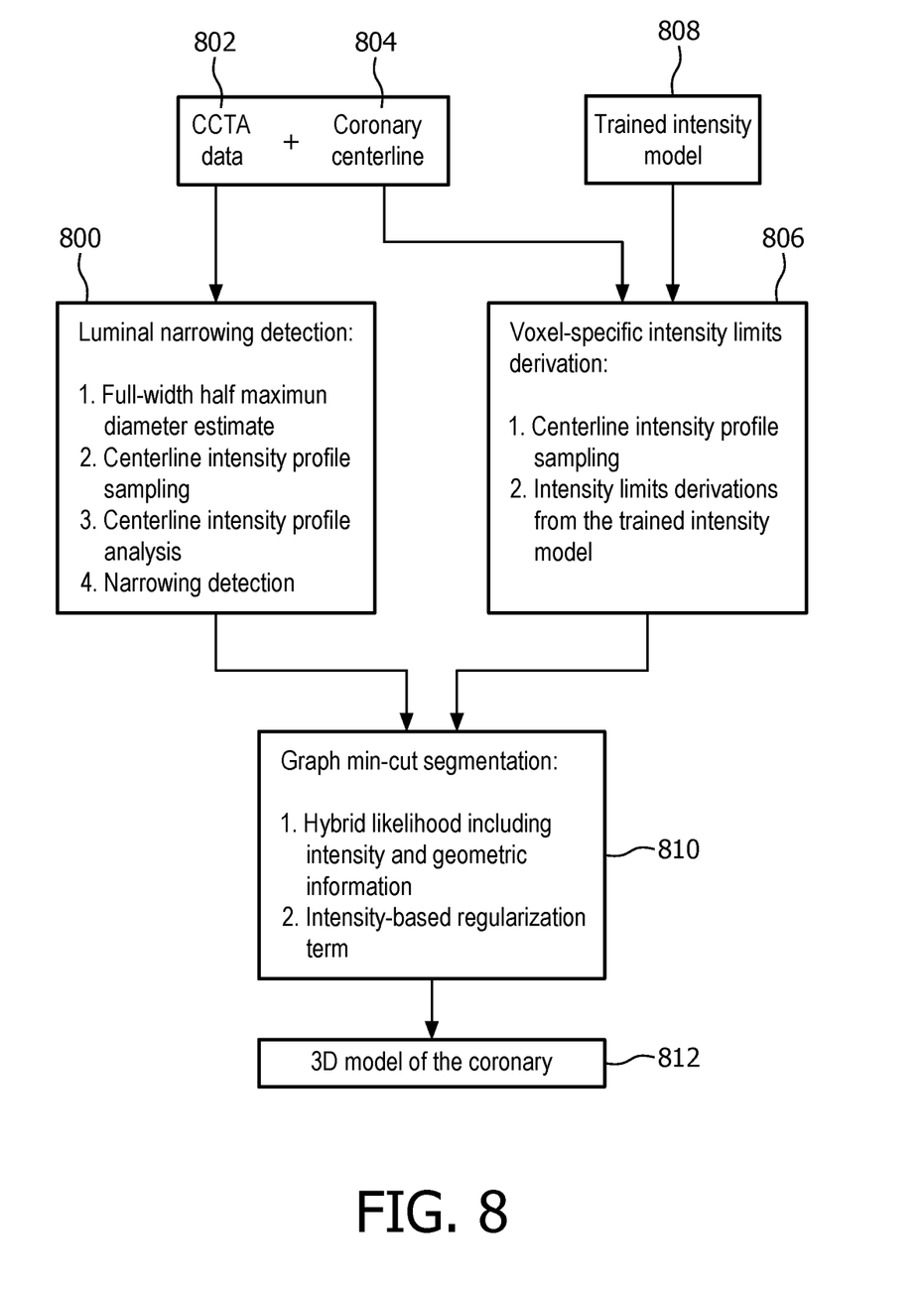
FIG. 8 flowcharts an example method of sub-resolution luminal narrowing detection and segmentation.

With reference to FIG. 8, an example method of sub-resolution luminal narrowing detection and segmentation is flowcharted. At 800, luminal narrowing is detected from the image data, such as CCTA data, and a vessel centerline, to compute a sub-resolution determined lumen diameter. A visible lumen diameter is approximated from the image data and the centerline using a FWHM rule and/or other approach. Intensity profiles are sampled at cross-sections along the centerline. Centerline intensity profiles are analyzed as described in reference to FIGS. 3, 4 and 5. Narrowing is detected as described in reference to FIGS. 4 and 5, which includes narrowing detected by intensity below a minimum threshold, and intensities above a maximum threshold. A sub-resolution determined diameter is computed for cross sections along the centerline based on the detected narrowing's and the approximated visible lumen diameter.

Voxel-wise intensity limits are derived at 806 from the centerline intensity profiles and the functions of the trained model. Examples of the functions of the trained model are described in reference to FIGS. 6 and 7.

At 810, a graph is constructed based on the voxel-wise intensity-based likelihoods, the voxel-wise diameter-based likelihoods, the smoothness penalty, and the optimization. The graph is cut into two portions by a min-cut segmentation algorithm. One portion defines the segmented lumen 812, and one portion is background, e.g. not segmented lumen. The segmented lumen 812 is represented as a three-dimensional spatial model, such as a coronary artery lumen.

Figure 9:
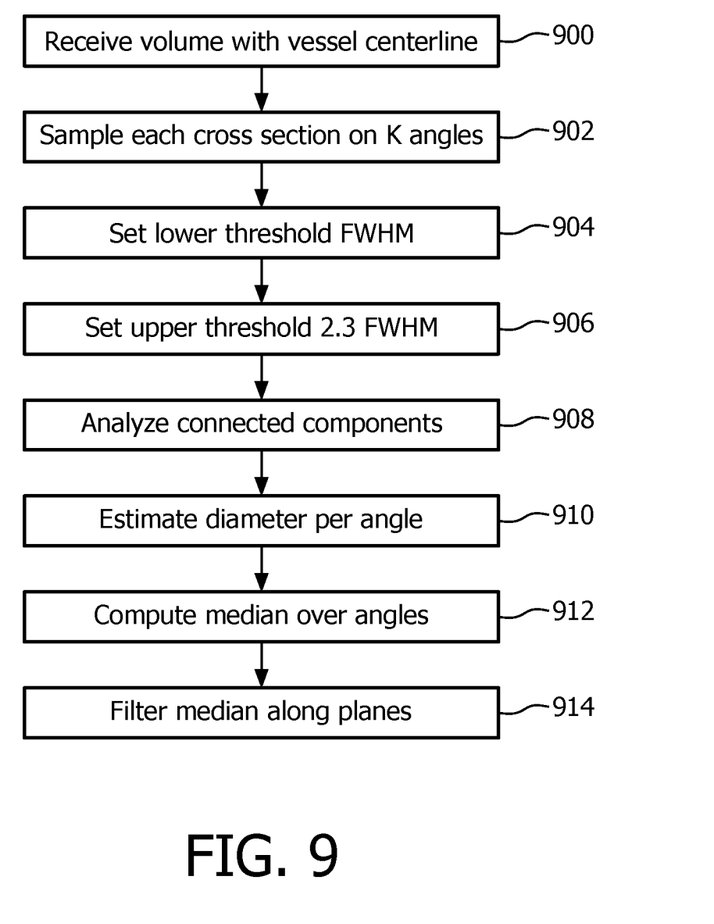
FIG. 9 flowcharts an example method of approximating a visible lumen diameter.

With reference to FIG. 9 an example method of approximating a visible lumen diameter is flowcharted. At 900, an image volume is received with a generated centerline of a vessel. Cross-sections are sampled along the centerline at 902. Each cross-section is sampled in rays of a plane of the cross-section, and the rays are at k angles, where k is an integer >0.

For each cross-section a lower threshold is computed using the FWHM rule at 904. For each cross-section an upper threshold is computed using a constant, such as 2.3, times the lower threshold at 906.

At 908, outliers, e.g. rays at an angle, are eliminated from each cross-section, which are below the lower threshold or upper threshold. Diameters are estimated for each remaining angle in a cross-section at 910.

An approximated visible diameter is computed, such as a median diameter, mean diameter, and the like, from the estimated diameters at the remaining angles for each cross-section at 912.

At 914, the approximated visible diameter at cross-sections along the centerline can be filtered. The filtering can use a smoothing filter, such as a averaging across cross-sections, which smooths the variations in the approximated diameter from cross-section to cross-section.

Figure 10:
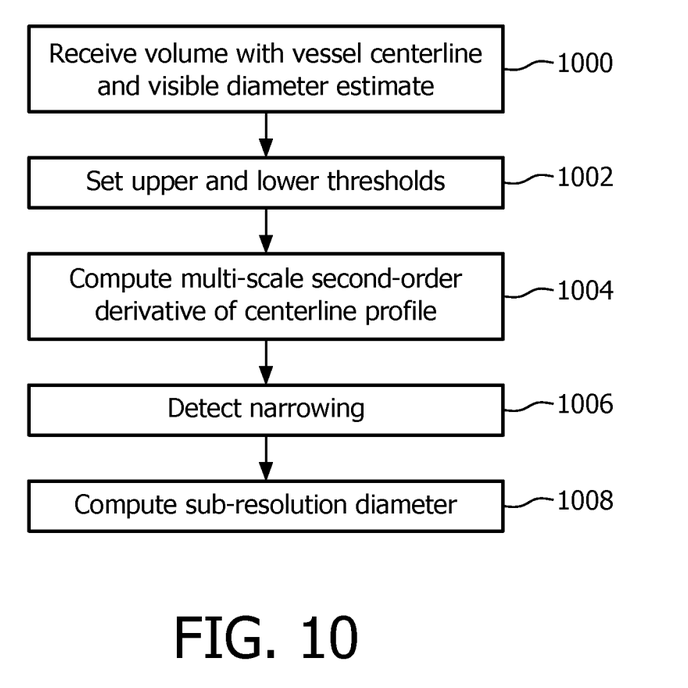
FIG. 10 flowcharts an example method of detecting sub-resolution luminal narrowing.

With reference to FIG. 10, an example method of detecting sub-resolution luminal narrowing is flowcharted. At 1000, an image volume is received with a generated vessel centerline and an approximated visible diameter of a lumen estimated.

At 1002, an upper intensity threshold and a lower intensity threshold are determined. The upper threshold can be determined from intensities of the aorta lumen. The lower threshold can be determined from intensities of the centerline.

A multi-scale second order derivative of the centerline profile is computed at 1004.

Narrowing is detected at 1006. Intensity values greater than the maximum threshold and with the second order derivative negative, e.g. local maxima, identify narrowing due to calcium blooming at cross-sections along the centerline. Intensity values less than the minimum threshold and with the second order derivative positive, e.g. local minima, identify the detected narrowing at cross-sections along the centerline based on intensity.

At 1008, the approximated visible diameter is modified based on the detected narrowing based on either the narrowing according to the reduced intensity, or the narrowing due to calcium blooming to compute the sub-resolution determined diameter at each cross-section.

The above may be implemented by way of computer readable instructions, encoded or embedded on computer readable storage medium, which, when executed by the data processor(s), cause the data processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system for detecting narrowing of a vessel lumen and segmenting the vessel lumen, comprising:
   one or more processors configured to:
      receive image data;
      generate a centerline through the vessel lumen from the image data;
      estimate a visible lumen diameter by approximating the image data and the centerline;
      detect, at a greater precision than a visible resolution of the imaging system, the narrowing of the vessel lumen in the image data using a centerline profile analysis, wherein the centerline profile analysis detects the narrowing of the vessel lumen based on intensity profiles that are lower than a predetermined minimum threshold or greater than a predetermined maximum threshold, the intensity profiles being obtained by sampling voxels in cross-sections along the centerline; and
      calculate sub-resolution diameters in the cross-sections along the centerline by modifying the estimated visible lumen diameter with the detected narrowing of the vessel lumen.

2. The imaging system according to claim 1, wherein the one or more processors are further configured to segment the vessel lumen of the image data into a first portion that represents the vessel lumen and a second portion that represents background, wherein each voxel in the first portion is assigned first and second values, wherein the first value indicates how likely for a voxel to be included in the first portion based on an intensity of a closest centerline voxel used by a trained model, and a second value indicates how likely for the voxel to be included in the first portion based on a spatial distance of the voxel from a closest centerline point and a sub-resolution diameter.

3. The imaging system according to claim 1, wherein the sub-resolution diameters are calculated based on diameters calculated using a full-width at half maximum intensity of the intensity profiles for each cross-section along the centerline of the vessel lumen.

4. The imaging system according to claim 2, wherein the trained model models characteristics of intensities of the voxels in the cross-sections along the centerline.

5. The imaging system according to claim 4, wherein the trained model includes a linear function fitted to a minimum threshold of intensities of the voxels in the cross sections along the centerline.

6. The imaging system according to claim 4, wherein the trained model includes a linear function fitted to a maximum threshold of intensities of the voxels in the cross sections along the centerline.

7. A method of detecting narrowing of a vessel lumen and segmenting the vessel lumen by an imaging system, comprising:
   receiving image data;
   generating a centerline through the vessel lumen from the image data;
   estimating a visible lumen diameter by approximating the image data and the centerline;
   detecting, at a greater precision than a visible resolution of the imaging system, the narrowing of the vessel lumen in the image data using a centerline profile analysis, wherein the centerline profile analysis detects the narrowing of the vessel lumen based on intensity profiles that are lower than a predetermined minimum threshold or greater than a predetermined maximum threshold, the intensity profiles being obtained by sampling voxels in cross-sections along the centerline; and
   calculating sub-resolution diameters in the cross-sections along the centerline by modifying the estimated visible lumen diameter with the detected narrowing of the vessel lumen.

8. The method according to claim 7, further comprising segmenting the vessel lumen of the image data into a first portion that represents the vessel lumen and a second portion that represents background, wherein each voxel in the first portion is assigned first and second values, wherein the first value indicates how likely for a voxel to be included in the first portion based on an intensity of a closest centerline voxel used by a trained model, and a second value indicates how likely for the voxel to be included in the first portion based on a spatial distance of the voxel from a closest centerline point and the sub-resolution diameter.

9. The method according to claim 7, wherein the sub-resolution diameters are calculated based on diameters calculated using a full-width at half maximum intensity of the intensity profiles for each cross-section along the centerline of the vessel lumen.

10. The method according to claim 7, wherein the trained model models characteristics of intensities of the voxels in the cross-sections along the centerline.

11. The method according to claim 10, wherein the trained model includes a linear function fitted to a minimum threshold of intensities of the voxels in the cross sections along the centerline.

12. The method according to claim 10, wherein the trained model includes a linear function fitted to a maximum threshold of intensities of the voxels in the cross sections along the centerline.

* * * * *